(12) United States Patent
Mosler

(10) Patent No.: US 6,740,125 B2
(45) Date of Patent: May 25, 2004

(54) KNEE-JOINT PROSTHESIS WITH A HYDRAULIC DAMPING CYLINDER

(75) Inventor: Luder Mosler, Duderstadt (DE)

(73) Assignee: Otto Bock Healthcare GmbH, Duderstadt (DE)

( * ) Notice: Subject to any disclaimer, the term of this patent is extended or adjusted under 35 U.S.C. 154(b) by 0 days.

(21) Appl. No.: 10/378,931

(22) Filed: Mar. 5, 2003

(65) Prior Publication Data

US 2003/0187517 A1 Oct. 2, 2003

(30) Foreign Application Priority Data

Mar. 28, 2002 (DE) ......................... 102 14 357

(51) Int. Cl.⁷ ................................. A61F 2/64
(52) U.S. Cl. ................. 623/45; 623/24; 188/267.1; 188/267.2
(58) Field of Search ............... 623/45, 39, 43, 623/44, 24; 188/266, 267, 267.1, 267.2, 140.14

(56) References Cited

U.S. PATENT DOCUMENTS

| | | | | |
|---|---|---|---|---|
| 4,053,952 A | * | 10/1977 | Goldstein | 623/26 |
| 5,277,281 A | * | 1/1994 | Carlson et al. | 188/267 |
| 6,378,558 B1 | * | 4/2002 | Pohl et al. | 137/827 |
| 6,443,993 B1 | * | 9/2002 | Koniuk | 623/24 |
| 2002/0133237 A1 | * | 9/2002 | Christesen | 623/24 |

FOREIGN PATENT DOCUMENTS

| | | |
|---|---|---|
| DE | 198 59 931 A1 | 7/2000 |
| GB | 2 111 171 A | 6/1983 |
| GB | 2 244 006 A | 11/1991 |

* cited by examiner

*Primary Examiner*—Bruce E Snow
(74) *Attorney, Agent, or Firm*—Whitham, Curtis & Christofferson, P.C.

(57) ABSTRACT

The invention relates to a knee-joint prosthesis with a hydraulic damping cylinder (1) for regulating the swing phase control and stance phase stabilization, and with an electronic control for a force field acting on the hydraulic fluid of the damping cylinder (1), the viscosity of the hydraulic fluid being able to be changed by the force field. The object of the present invention is to make available a knee-joint prosthesis whose electronic control has a high degree of safety and a minimal power consumption. According to the invention, the object is achieved by the fact that an actuating member (6, 7, 9, 12) is provided which generates a permanent force field and acts on the hydraulic fluid with an existing force field which is weakened or strengthened by the electronically controlled force field.

12 Claims, 3 Drawing Sheets

KNEE-JOINT PROSTHESIS WITH A HYDRAULIC DAMPING CYLINDER

BACKGROUND

The invention relates to a knee-joint prosthesis with a hydraulic damping cylinder as set forth in the preamble of claim 1. The damping properties of a hydraulic cylinder for use in a prosthetic knee can be designed to be controllable in order to take account of the different resistance demands in the swing phase and the stance phase. One possibility of adaptation lies in electronic control via electrical actuating members which either change the current conditions or affect the viscosity properties of the fluid. A change in current conditions can be effected via a regulator valve, and a change in viscosity properties can be effected by acting, for example, on magnetorheological fluids.

As regards changing the viscosity properties of a fluid, it is known from the prior art for an actuating member, as a function of the phase of movement, to change the viscosity of the fluid by application of a magnetic field, with a high resistance and consequently a high viscosity being necessary in particular in the stance phase. Since the stance phase generally lasts longer than the swing phase, a relatively high current is always needed to safely permit standing.

SUMMARY

Starting from this prior art, the object of the invention is to make available a knee-joint prosthesis which can be controlled with lower power consumption and which additionally guarantees increased safety in the event of the control system failing.

According to the invention, this object is achieved by a knee-joint prosthesis with the features of claim 1.

Advantageous embodiments and developments of the invention are set out in the dependent claims.

By means of an actuating member which generates a permanent force field and acts on the hydraulic fluid with an existing force field which is weakened or strengthened by the electronically controlled force field, only a low current need be applied for the swing phase in order to weaken the existing force field via the electronically controlled force field or to increase stance safety by means of an electronically controlled force field correspondingly differently oriented. In the event of a failure of the electronic control system, the stance stability of the prosthesis wearer is thus further guaranteed and a movement possibility, albeit a limited one, remains. In addition, the maintenance intervals for the knee-joint prosthesis can be extended, since overall there is a lower power consumption.

One embodiment of the invention involves a premagnetized actuating member which acts on a magnetorheological hydraulic fluid with a magnetic field.

In order to provide a constant magnetic field, the actuating member advantageously has a permanent magnet whose magnetic field is strengthened or weakened via a suitably arranged magnet coil to which voltage is applied.

As an alternative to this, provision is made for the force field to be an electrical field and for the hydraulic fluid to be an electrorheological fluid, the actuating member having electrodes made of an electret.

A particularly compact construction of the knee-joint prosthesis and of the damping device is obtained if the actuating member is located inside a piston or is integrated in the latter, which piston moves in the damping cylinder so that no additional structural space is needed to accommodate the actuating member. In a development of the magnetorheological variant, provision is made for the damping cylinder to be made of a ferromagnetic material in order to achieve a higher degree of integration.

In a further development, provision is made for a passage for the movement of the hydraulic fluid to be present between the inside wall of the cylinder and the hydraulic piston, so that the cylinder wall forms part of the magnetic circuit or the field excitation closed by the piston, the embedded permanent magnet or electrets via the passage and the cylinder. The passage is advantageously designed as an annular gap so that leakage takes place around the piston.

As an alternative to this, a passage for the movement of the magnetorheological or electrorheological fluid is formed inside the piston, so that the magnetic circuit or the field closes inside the piston and there changes the viscosity of the fluid flowing through. In this embodiment, it is not necessary for the cylinder to be made of a ferromagnetic material. The passage can be designed as a bore, channel or annular gap with diamagnetic bridges for magnetorheological fluids, in which case a plurality of bores or channels can also be formed inside the piston or at the piston edge.

An advantageous form of energy supply to the actuating member consists of a feed line through the piston rod, by which means the energy can be fed in a very stable manner and immediately to the magnet coil or the electrodes inside the piston.

In another embodiment of the invention, it is provided that the cylinder volumes which can be changed by the hydraulic piston are connected via a connecting line or leakage line and the actuating member acts on the magnetorheological or electrorheological fluid in the leakage line or connecting line with a field or changes the existing field in the line. Such an arrangement involves a relatively low outlay in construction terms and can be realized with conventional hydraulic means and field-generating elements.

The invention is explained in more detail below on the basis of illustrative embodiments. Identical reference numbers in different figures designate identical structural elements.

DESCRIPTION OF THE DRAWINGS

FIG. 2a shows a damper unit with an actuating member integrated in a piston;

FIG. 2b shows a variant of the damper unit according to FIG. 2a; and

DETAILED DESCRIPTION OF THE INVENTION

FIGS. 1, 2a, 2b, and 3 shown generally a knee joint prosthesis 15a–c according to the present invntion.

Figure 1:
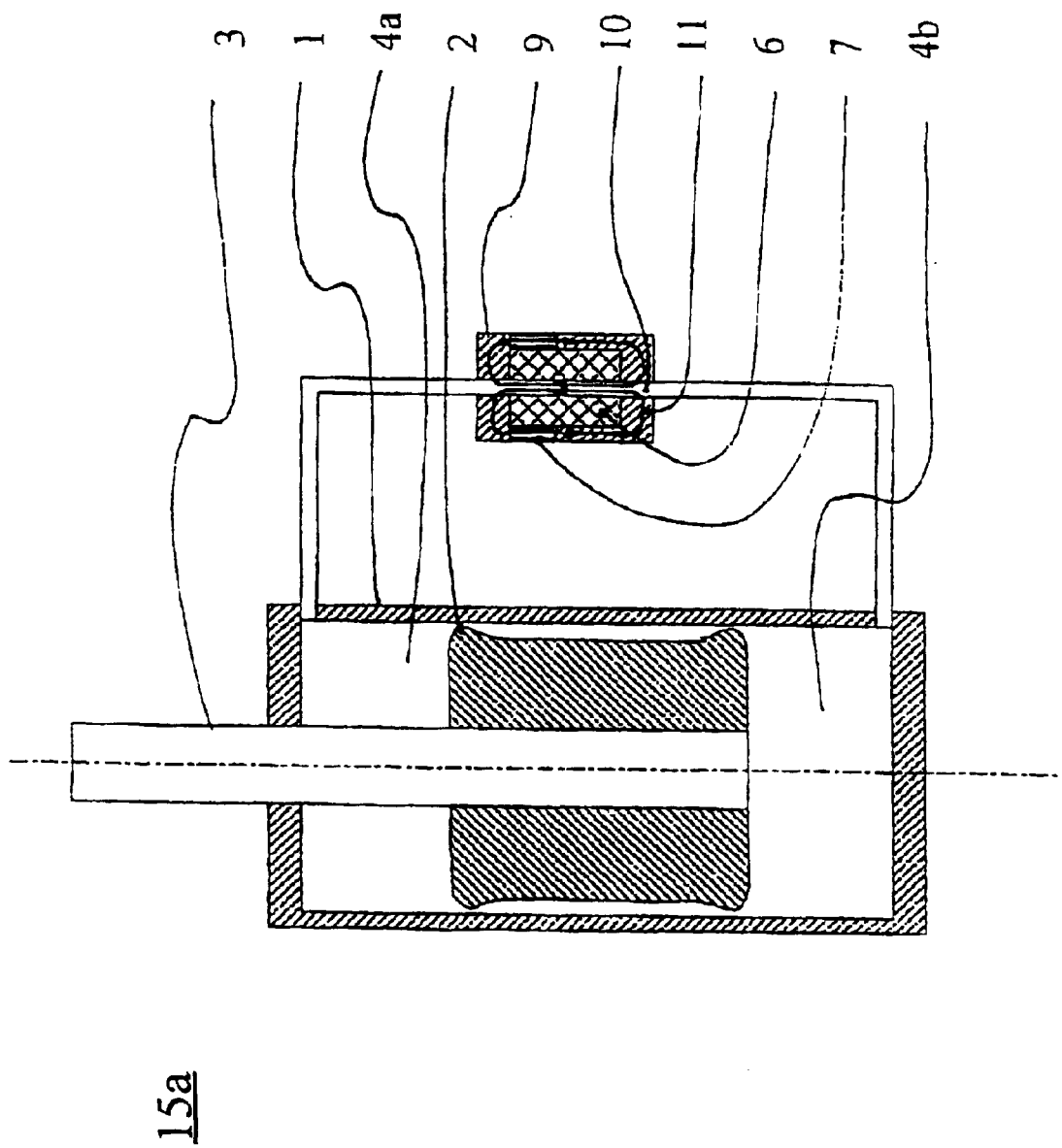
FIG. 1 shows a first embodiment of a damper unit with an external actuating member.

FIG. 1 is a cross-sectional representation of a hydraulic damping cylinder 1 with a hydraulic piston 2 which moves in the latter and which is moved in an oscillating manner via a piston rod 3 inside the cylinder 1. Provided at the dead centers of the piston 2 there is in each case an attachment for a leakage line 10 which connects the changing cylinder volumes 4a, 4b to one another. Upon a movement of the piston 2 inside the cylinder 1, a magnetorheological fluid present inside the cylinder 1 is thus pumped through the leakage line 10. Arranged around the leakage line 10 there is a permanent magnet 7 inside which there is an electronically controllable magnet coil 6 which is enclosed by pole plates 9 in order to realize a closed magnetic circuit 11 when a voltage is applied. The magnetic circuit 11 encloses the leakage line 10. Depending on the orientation of the magnetic field generated by the magnet coil 6, the magnetic field formed by the permanent magnet 7 and always present is strengthened or weakened so as to correspondingly change the viscosity properties of the magnetorheological fluid. The permanent magnet 7 provides for premagnetization, with which a certain damping is preset. As a result of this presetting, a more favorable energy consumption can be achieved on the basis of small additional magnetic fields via the magnet coil 6.

Thus, in addition to a presetting to a basic damping value, the damping is electronically controlled by a change in the magnetic excitation via the magnet coil 6, by which means the magnetorheological fluid constituting the hydraulic medium is correspondingly influenced.

Figure 2:
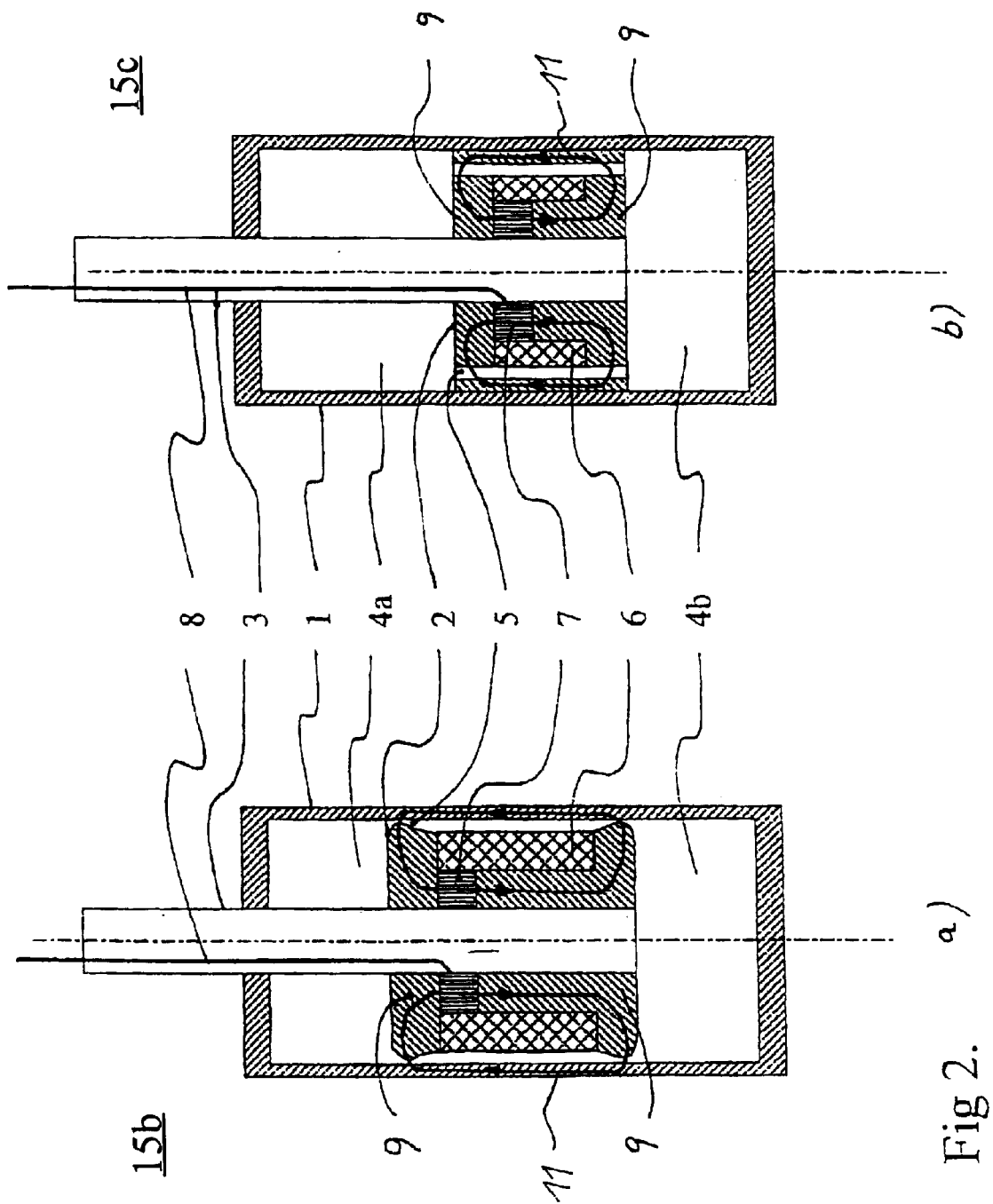

As an alternative to this, provision is made for a closed embodiment of the damper unit, in which the leakage between the cylinder volumes 4a, 4b occurs inside the cylinder 1. FIG. 2a shows a first variant in which a passage 5 in the form of an annular gap is formed between the piston 2 and the inside wall of the cylinder, so that the magnetorheological fluid flows through the annular gap 5 upon a movement of the piston 2 inside the cylinder 1. Formed inside the piston 2 there is a permanent magnet 7 which provides for premagnetization, which is effected by the ferromagnetic piston 2, which forms the pole plates 9 for the magnet coil 6, and the ferromagnetic cylinder wall, so that a closed magnetic circuit 11 is formed inside these components. By means of the premagnetization obtained via the permanent magnet 7, a certain degree of damping is preset, which is strengthened by activation of the magnet coil 6 via a feed line 8 routed through the piston rod 3, or is decreased in the case of a correspondingly different orientation. In this way, the degrees of damping of the knee-joint prosthesis can be adjusted over a wide range.

For the case where the cylinder 1 is not ferromagnetic and, consequently, the magnetic circuit cannot be closed via the ferromagnetic piston 2 with embedded permanent magnet 7 via the annular gap 5 and the ferromagnetic cylinder 1, a variant is shown in FIG. 2b in which the leakage takes place through the piston 2, the leakage flow being formed by a passage 5, for example in the form of a bore, a channel or an interrupted annular gap. The piston 2 is thus sealed off against the inside wall of the cylinder so that a leakage flow takes place only through the passage 5 provided inside the piston 2, said passage 5 being provided with diamagnetic bridges. The magnetic circuit 11 is thus established in the piston 2, said magnetic circuit 11 in the present embodiment being formed by the permanent magnet 7 and the piston 2. If need be, the magnetic circuit 11 or magnetic field can be strengthened or weakened by activation of the magnet coil 6. The feed line to the magnet coil 6 is once again routed through the piston rod 3, so that safe and reliable control of the magnet coil 6 is guaranteed.

The damping cylinder 1 is therefore a hydraulic cylinder which is provided with a specific leakage between the two cylinder volumes 4a, 4b, which are separated by the hydraulic piston 2. The leakage rate is controlled by means of the magnetorheological fluid, which constitutes the hydraulic medium, being acted upon by a magnetic field which is initially provided by a permanent magnet 7 and thus affords a premagnetization of the magnetorheological fluid and presetting of the damping. If need be, the damping can be controlled electronically by applying a voltage to the magnet coil 6, that is to say the viscosity of the hydraulic medium is changed and, consequently, the damping.

To reduce the number of components, provision is made for the pole plates 9 to be formed by the piston 2 itself, in which case the piston 2 is made of a ferromagnetic material with an embedded permanent magnet 7 or a plurality of embedded permanent magnets 7.

Figure 3:
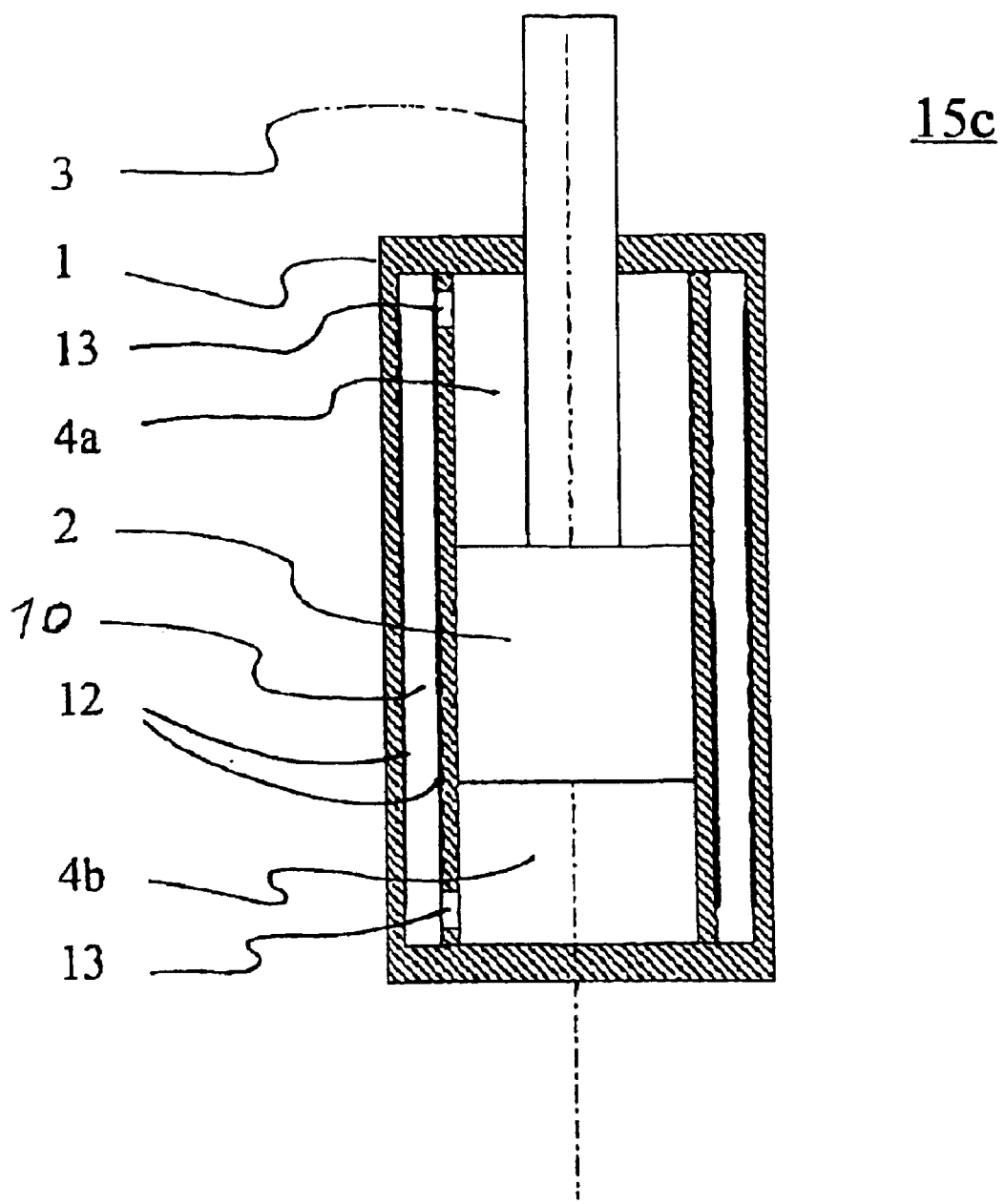
FIG. 3 shows an embodiment of the damper unit for electrorheological fluids.

A possible embodiment of the one damping cylinder 1 with an electrorheological hydraulic fluid is shown in FIG. 3.

The leakage between the cylinder volumes 4a and 4b is in this case effected via circumferential bores 13 and a leakage line 10 arranged concentrically with respect to the cylinder 1. This carries the planar electrodes 12. When these are acted upon with an electrical potential field, the viscosity of the electrorheological fluid rises, which increases the resistance to the displacement of the piston 2. According to the invention, these electrodes 12 can be designed as electrically prepolarized electret.

In none of the embodiments is account taken of the fact that the piston surface of the upper cylinder volume 4a is reduced by the surface of the piston rod 3, and thus a volume compensation or a continuous piston rod 3 is required. Such compensation volumes, as gas-prestressed or spring-prestressed solutions, belong to the prior art and are not included here for reasons of clarity.

What is claimed is:

1. Knee-joint prosthesis, comprising a hydraulic damping cylinder for regulating the swing phase control and stance phase stabilization, and an electronic control for a force field acting on the hydraulic fluid of the damping cylinder, the viscosity of the hydraulic fluid being able to be changed by the force field, wherein an actuating member which generates a permanent force field and acts on the hydraulic fluid with an existing force field which is weakened or strengthened by the electronically controlled force field.

2. Knee-joint prosthesis according to claim 1, wherein the force field is a magnetic field and the hydraulic fluid is a magnetorheological fluid.

3. Knee-joint prosthesis according to claim 1, wherein the actuating member has a permanent magnet and a magnet coil.

4. Knee-joint prosthesis according to claim 3, wherein the damping cylinder (1) is made of a ferromagnetic material.

5. Knee-joint prosthesis according to claim 1, wherein the force field is an electric field and the hydraulic fluid is an electrorheological fluid.

6. Knee-joint prosthesis according to claim 5, wherein the actuating member has electrodes made of an electret.

7. Knee-joint prosthesis according to claim 1, wherein the actuating member is arranged in a piston moving inside the damping cylinder.

8. Knee-joint prosthesis according to claim 7, wherein a passage for the movement of the hydraulic fluid is formed in the piston or between the inside wall of the cylinder and the piston.

9. Knee-joint prosthesis according claim 7, wherein the passage is designed as an annular gap.

10. Knee-joint prosthesis according to claim 9, wherein the passage is designed as a bore, channel or annular gap with diamagnetic bridges.

11. Knee-joint prostheses according to claim 1, wherein a feed line to the actuating member extends through a piston rod.

12. Knee-joint prosthesis according to claim 1, wherein the cylinder volumes which can be changed by a piston are connected via a leakage line and the actuating member acts on the magnetorheological fluid in the leakage line with a magnetic field or electric field.

* * * * *